(12) United States Patent
Hur et al.

(10) Patent No.: US 10,022,082 B2
(45) Date of Patent: Jul. 17, 2018

(54) APPARATUS AND METHOD FOR DETECTING A STATE OF A DRIVER BASED ON BIOMETRIC SIGNALS OF THE DRIVER

(71) Applicants: HYUNDAI MOTOR COMPANY, Seoul (KR); KIA MOTORS CORPORATION, Seoul (KR); GWANGJU INSTITUTE OF SCIENCE AND TECHNOLOGY, Buk-gu, Gwangju (KR)

(72) Inventors: Nam Woong Hur, Hwaseong-si (KR); Seul Ki Jeon, Suwon-si (KR); Hyun Sang Kim, Hwaseong-si (KR); Eung Hwan Kim, Seoul (KR); Sang Tae Ahn, Gwangju (KR); Hyo Jung Jang, Gimpo-si (KR); Sung Chan Jun, Gwangju (KR)

(73) Assignees: Hyundai Motor Company, Seoul (KR); Kia Motors Corporation, Seoul (KR); Gwangju Institute of Science and Technology, Gwangju (KR)

( * ) Notice: Subject to any disclaimer, the term of this patent is extended or adjusted under 35 U.S.C. 154(b) by 84 days.

(21) Appl. No.: 15/356,083

(22) Filed: Nov. 18, 2016

(65) Prior Publication Data

US 2017/0367635 A1   Dec. 28, 2017

(30) Foreign Application Priority Data

Jun. 27, 2016   (KR) ........................ 10-2016-0080410

(51) Int. Cl.
*A61B 5/18*   (2006.01)
*A61B 5/0478*   (2006.01)
(Continued)

(52) U.S. Cl.
CPC .............. *A61B 5/18* (2013.01); *A61B 5/0261* (2013.01); *A61B 5/0402* (2013.01);
(Continued)

(58) Field of Classification Search
CPC ....... A61B 5/18; A61B 5/0261; A61B 5/0402; A61B 5/0478; A61B 5/024; A61B 5/026; G08B 23/00
(Continued)

(56) References Cited

U.S. PATENT DOCUMENTS

| 8,725,311 B1 * | 5/2014 | Breed .................... G08B 21/06 600/300 |
| 9,873,437 B2 * | 1/2018 | Fung ..................... B60W 40/08 |

(Continued)

FOREIGN PATENT DOCUMENTS

| JP | 2004-110546 | 4/2004 |
| JP | 2006-280512 A | 10/2006 |

(Continued)

*Primary Examiner* — Hung T Nguyen
(74) *Attorney, Agent, or Firm* — Brinks Gilson & Lione

(57) ABSTRACT

An apparatus and a method is provided for detecting biometric signals of a driver and classifying the driver into a normal state or a fatigued state based on the biometric signals. An apparatus may include: a biometric signal measuring part configured to measure the biometric signals including a blood flow rate of a brain of the driver using an electro-encephalography (EEG), an electro-cardiography (ECG), and a functional near-infrared spectroscopy (fNIRS) of the driver; a biometric signal integral part configured to integrate the measured biometric signals, to extract characteristics of the respective biometric signals from the measured biometric signals and to then integrate the extracted characteristics, or to classify the extracted characteristics of the biometric signals and to then integrate the classified characteristics; and a driver state detecting part configured to (Continued)

detect the state of the driver based on the integrated biometric signals.

11 Claims, 10 Drawing Sheets

(51) Int. Cl.
    *A61B 5/04*         (2006.01)
    *A61B 5/0402*     (2006.01)
    *A61B 5/0476*     (2006.01)
    *A61B 5/026*      (2006.01)

(52) U.S. Cl.
    CPC ........ *A61B 5/04012* (2013.01); *A61B 5/0476* (2013.01); *A61B 5/0478* (2013.01)

(58) Field of Classification Search
    USPC ..... 340/575, 576; 600/300, 509, 529; 701/1, 701/45
    See application file for complete search history.

(56) References Cited

U.S. PATENT DOCUMENTS

| | | |
|---|---|---|
| 2007/0010754 A1 | 1/2007 | Muller et al. |
| 2010/0109881 A1* | 5/2010 | Eskandarian ........ A61B 5/6887 340/575 |
| 2012/0101690 A1* | 4/2012 | Srinivasan ........... A61B 5/0408 701/45 |
| 2015/0265201 A1* | 9/2015 | Arbas ...................... A61B 5/18 600/301 |

FOREIGN PATENT DOCUMENTS

| | | |
|---|---|---|
| JP | 2014-167438 | 9/2014 |
| KR | 10-2012-0068625 | 6/2012 |
| KR | 10-2014-0022312 | 2/2014 |
| KR | 10-2014-0096609 | 8/2014 |
| KR | 10-2014-0127977 | 11/2014 |
| KR | 10-2015-0012104 | 2/2015 |
| KR | 10-2015-0078476 | 7/2015 |
| KR | 10-2016-0018134 A | 2/2016 |

* cited by examiner

APPARATUS AND METHOD FOR DETECTING A STATE OF A DRIVER BASED ON BIOMETRIC SIGNALS OF THE DRIVER

CROSS-REFERENCE TO RELATED APPLICATION

This application is based on and claims the benefit of priority to Korean Patent Application No. 10-2016-0080410, filed on Jun. 27, 2016 in the Korean Intellectual Property Office, the entire disclosure of which is hereby incorporated by reference.

TECHNICAL FIELD

The present disclosure relates to an apparatus and a method for detecting a state of a driver based on biometric signals of the driver, and more particularly, to a technology of detecting biometric signals of a driver using a blood flow rate of brain, an electro-encephalography (EEG), and an electro-cardiography (ECG) of the driver.

BACKGROUND

Drivers that drive while drowsy, or fall asleep while driving, are a significant cause of traffic accidents. To prevent this drowsy driving, various methods and apparatuses have recently been studied.

For example, after an image is analyzed by observing and sensing physical changes of the driver, that is, a motion of an eyelid, a gaze direction of an eye, a nod, and the like using a camera to sense when the driver is drowsy, if the sensed image has a predetermined value or more, it is determined that the driver is in a state of drowsy driving, and warns the drowsy driving of the drowsiness, thereby preventing the drowsy driving.

Another method is determining whether or not the driver is in the state of drowsy driving by sensing and analyzing various biometric signals of the driver to determine a drowsy or sleeping state of the driver.

That is, there is a method for measuring and analyzing an electro-encephalography (EEG), electro-oculography (EGG), an electro-cardiography (ECG), and the like of the driver.

A physical state and a mental state of the driver described above may be detected by fine current signals flowing in both hands of the driver using an ECG sensor and a galvanic skin resistance (GSR) sensor, and may be more directly detected by fine current signals which may be detected from a skin around a head of the driver when a brain of the driver is active using an EEG sensor and an EGG sensor.

In particular, when the EEG sensor and the EGG are used, a drowsy driving situation of the driver or a state in which an attention of the driver is distracted may be sensed by a change in the electro-encephalography and the electro-oculography of the driver.

However, even in the case in which biometric signals of the driver are collected using a variety of sensors, when noise is mixed in the collected biometric signals, there is a problem that it is difficult to accurately determine the state of the driver. Therefore, in order to accurately diagnose a drowsy state and an emotion state of the driver and provide feedback on these states to the driver, it is required to collect the biometric signals of the driver from which surrounding environment factors (e.g., noise, etc.) are removed.

SUMMARY

The present disclosure has been made to address the above-mentioned problems occurring in the prior art while maintaining advantages achieved by the prior art.

An aspect of the present disclosure provides an apparatus and a method for detecting biometric signals of a driver capable of classifying and analyzing the driver into a normal state and a fatigued state using a blood flow rate of a brain, an electro-encephalography (EEG), and an electro-cardiography (ECG) of the driver to thereby quantify a fatigue level of the driver using the analyzed biometric signals.

Other objects and advantages of the present disclosure can be appreciated by the following description and will be clearly described by the exemplary embodiments of the present disclosure. It will be easily known that the objects and advantages of the present disclosure can be implemented by means and a combination thereof shown in the appended claims.

In an exemplary form of the present disclosure, an apparatus for detecting a state of a driver based on biometric signals of the driver includes: a biometric signal measuring part configured to measure the biometric signals including a blood flow rate of a brain of the driver using an electro-encephalography (EEG), an electro-cardiography (ECG), and a functional near-infrared spectroscopy (fNIRS) of the driver; a biometric signal integral part configured to integrate the measured biometric signals, to extract characteristics of the respective biometric signals from the measured biometric signals and to then integrate the extracted characteristics, or to classify the extracted characteristics of the biometric signals and to then integrate the classified characteristics; and a driver state detecting part configured to detect the state of the driver based on the integrated biometric signals.

The biometric signal measuring part may include: an electro-encephalography measuring apparatus configured to measure the electro-encephalography occurring from the brain; an emitter configured to generate near-field infrared ray to measure the blood flow rate of the brain; and a detector configured to detect the near-field infrared ray reflected after the emitter generates the near-field infrared ray and to obtain electrical signals.

When characteristics of the respective biometric signals are extracted from the measured biometric signals, characteristics of the electro-encephalography may be extracted by extracting characteristics of a relative power level (RPL) using electrodes attached to a scalp of the driver.

When characteristics of the respective biometric signals are extracted from the measured biometric signals, characteristics of the electro-cardiography may be extracted by extracting a component of R among components of P, Q, R, S, and T of the electro-cardiography and calculating a heart rate using the extracted component of R.

When characteristics of the respective biometric signals are extracted from the measured biometric signals, the blood flow rate of the brain of the driver may be measured by measuring a reflection amount by a detector, converting light intensity into oxyhemoglobin and specific oxyhemoglobin concentrations using an absorption rate of light, and using the oxyhemoglobin and specific oxyhemoglobin concentrations.

The driver state detecting part may calculate a driving condition level by applying the same weight to values of the electro-encephalography, the electro-cardiography, and the blood flow rate of the brain.

In another exemplary form of the present disclosure, a method for detecting a state of a driver based on biometric signals of the driver includes: measuring the biometric signals including a blood flow rate of a brain of the driver using an electro-encephalography (EEG), an electro-cardiography (ECG), and a functional near-infrared spectroscopy (fNIRS) of the driver; integrating the measured biometric signals, extracting characteristics of the respective biometric signals from the measured biometric signals and then integrating the extracted characteristics, or classifying the extracted characteristics of the biometric signals and then integrating the classified characteristics; and detecting the state of the driver based on the integrated biometric signals.

When characteristics of the respective biometric signals are extracted from the measured biometric signals, characteristics of the electro-encephalography may be extracted by extracting characteristics of a relative power level (RPL) using electrodes attached to a scalp of the driver.

When characteristics of the respective biometric signals are extracted from the measured biometric signals, characteristics of the electro-cardiography may be extracted by extracting a component of R among components of P, Q, R, S, and T of the electro-cardiography and calculating a heart rate using the extracted component of R.

When characteristics of the respective biometric signals are extracted from the measured biometric signals, the blood flow rate of the brain of the driver may be measured by measuring a reflection amount by a detector, converting light intensity into oxyhemoglobin and specific oxyhemoglobin concentrations using an absorption rate of light, and using the oxyhemoglobin and specific oxyhemoglobin concentrations.

A driving condition level may be calculated by applying the same weight to values of the electro-encephalography, the electro-cardiography, and the blood flow rate of the brain.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
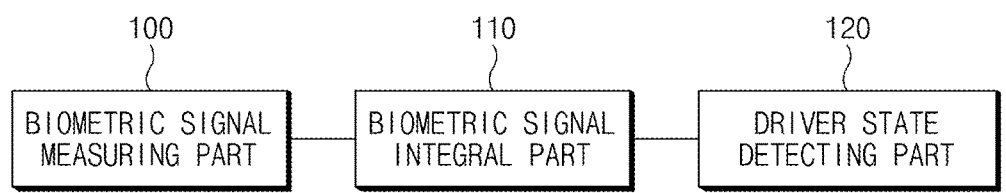
FIG. 1 is a configuration diagram, illustrating an apparatus for detecting a state of a driver based on biometric signals of the driver.

Advantages and features of the present disclosure and methods to achieve them will be described from exemplary forms described below in detail with reference to the accompanying drawings. However, the present disclosure is not limited to the exemplary forms set forth herein, but may also be modified in many different forms. Merely, the exemplary forms of the present disclosure will be provided to describe the spirit of the present disclosure in detail so that those skilled in the art may easily implement the spirit of the present disclosure.

In the drawings, the exemplary forms of the present disclosure are not limited to illustrated specific forms, but are exaggerated for clarity. In the present specification, specific terms have been used, but are just used for the purpose of describing the present disclosure and are not used for qualifying the meaning or limiting the scope of the present disclosure, which is disclosed in the appended claims.

In the present specification, an expression 'and/or' is used as a meaning including at least one of components listed before and after the expression. In addition, an expression 'connected to/coupled to' is used as a meaning including a case in which one component is directly connected to another component or is indirectly connected through another component. Unless explicitly described to the contrary, a singular form includes a plural form in the present specification. In addition, components, steps, operations, and elements mentioned by 'comprise' or 'comprising' used in the present specification mean the existence or addition of one or more other components, steps, operations, and elements.

Hereinafter, exemplary forms of the present disclosure will be described in detail with reference to the accompanying drawings.

FIG. 1 is a configuration diagram illustrating an apparatus for detecting a state of a driver based on biometric signals of the driver.

Referring to FIG. 1, the apparatus for detecting a state of a driver based on biometric signals of the driver includes a biometric signal measuring part 100, a biometric signal integral part 110, and a driver state detecting part 120.

The biometric signal measuring part 100 measures the biometric signals including a blood flow rate of a brain of the driver using an electro-encephalography (EEG), an electro-cardiography (ECG), and a functional near-infrared spectroscopy (fNIRS) of the driver.

The electro-encephalography (EEG), which is a flow of electricity occurring when a signal is transferred between brain nerves in a nervous system of the driver, is an important indicator of measuring activity of a brain because it differently exhibits depending on a state of mind and body of the driver. The above-mentioned electro-encephalography may be measured by electrodes attached to a scalp of the driver, as a neurophysiological measuring method for electrical activity of the brain.

The ECG, which is an indicator analyzing electrical activity of a heart of a human for a defined time, plays an important role in determining a ratio and a constant period of heart beat, a size and a location of the heart, whether or not the heart is damaged, or the like. The ECG may be measured by electrodes attached to a skin of the driver and an external equipment connected to a body of the driver.

According to the fNIRS, near-infrared ray having a waveform of a range of 800 nm to 1300 nm which is present between visible ray and mid infrared ray spectrographed on a surface of the scalp through a spectroscope attached to the scalp of the driver, and the ray transmits through the scalp so as to be absorbed according to oxygen saturation of a blood flow. When the ray is measured by a measurer attached to be distant by a predetermined distance, the oxygen saturation of the blood flow may be calculated according to an absorption rate of ray, and hemodynamic information on activities of neurons of brain and activity of the brain associated therewith may be obtained.

In the biometric signal measuring part 100, the biometric signals measured using a biometric signal measuring apparatus configure data packets according to a data packet structure programmed in a main control unit (MCU) of hardware, and are transmitted to a personal computer (PC) at a rate of 250 Kbit per second through a Zigbee communication network. Software installed in the personal computer (PC) may receive the data packets of the biometric signals and output the biometric signals to a screen through a conversion algorithm, and the biometric signals may be stored in the main control unit (MCU) in a matrix structure in which channel and time forms are combined.

The biometric signal integral part 110 analyzes the measured biometric signals of the driver, and integrates the analyzed biometric signals.

The biometric signal integral part 110 may measure the biometric signals using multi-modality which measures various kinds of biometric signals at a time or simultaneously.

For example, the biometric signal integral part 110 integrates biometric signal data measured by the biometric signal measuring part 100 to utilize the integrated biometric signal data, simultaneously measures the respective biometric signals (the electro-encephalography (EEG), the electro-cardiography (ECG), the blood flow rate of brain, etc.) and then each extracts characteristics that best represent properties of the respective biometric signals, and integrates the extracted characteristics into one to generate data having high reliability.

Here, after the extracted characteristics which may best represent the properties of the biometric signals are classified by various kinds of classifier, a final output value of the various kinds of classifiers may be integrated into one.

The driver state detecting part 120 detects a state of the driver based on the integrated biometric signals.

Figure 2:
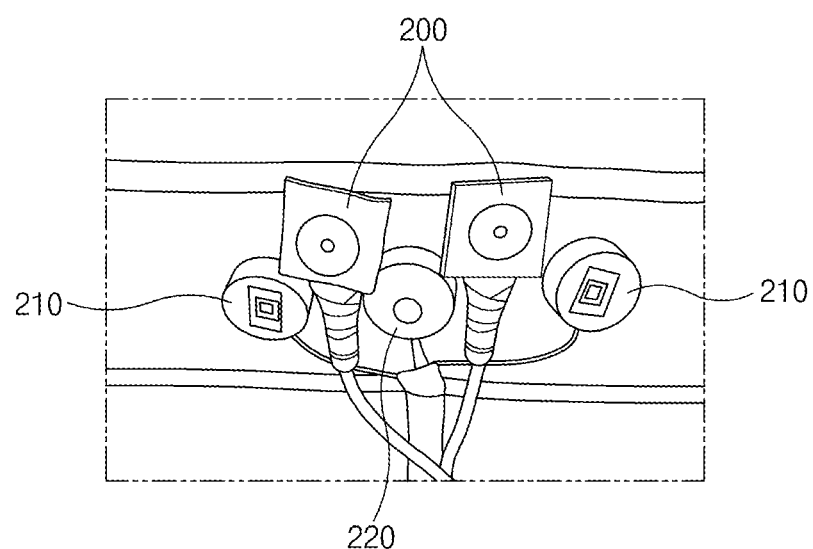
FIG. 2 is a diagram illustrating a biometric signal measuring part within the apparatus for detecting a state of a driver.

FIG. 2 is a diagram illustrating a biometric signal measuring part within the apparatus for detecting a state of a driver.

Referring to FIG. 2, in the biometric signal measuring part 100, the biometric signals measured using a biometric signal measuring apparatus configure data packets according to a data packet structure programmed in a main control unit (MCU) of hardware, and are transmitted to a personal computer (PC) at a rate of 250 Kbit per second through a Zigbee communication network. Software installed in the personal computer (PC) may receive the data packets of the biometric signals and output the biometric signals a screen through a conversion algorithm, and the biometric signals may be stored in the main control unit (MCU) in a matrix structure in which channel and time forms are combined.

For example, the biometric signal measuring part 100 includes an electro-encephalography measuring apparatus 200, a detector 210, and an emitter 220 in order to measure an electro-encephalography.

The electro-encephalography measuring apparatus 200 measures (EEG measures) electrical signals occurring from the brain on the scalp.

The detector 210 is an apparatus capable of obtaining the electrical signals by detecting near-field infrared ray reflected after the emitter 220 generates the near-field infrared ray to measure the blood flow rate of the brain.

The above-mentioned detector 210 may be referred to as a near-field infrared detector or a photon detector.

The emitter 220 is a near-field infrared generation apparatus for measuring the blood flow rate of the brain. For example, the emitter 220 may include a light emitting diode (LED).

Figure 3:
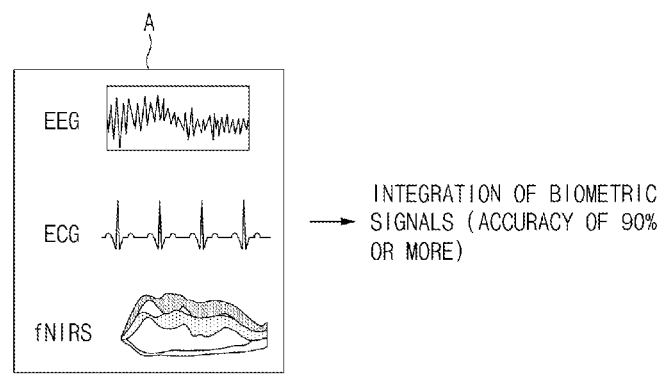
FIG. 3 is a diagram illustrating a biometric signal integral part within the apparatus for detecting a state of a driver.

FIG. 3 is a diagram illustrating a biometric signal integral part within the apparatus for detecting a state of a driver.

Referring to FIG. 3, the biometric signal integral part may measure the biometric signals using multi-modality A which measures various kinds of biometric signals at a time or simultaneously.

The biometric signal integral part may integrate the biometric signals measured by the biometric signal measuring part, extract characteristics of the biometric signals from the biometric signals measured by the biometric signal measuring part and then integrate the extracted characteristics, or classify the extracted characteristics of the biometric signals and then integrate the classified characteristics.

For example, the biometric signal integral part integrates the measured biometric signal data to utilize the integrated biometric signal data, simultaneously measures the respective biometric signals (the electro-encephalography (EEG), the electro-cardiography (ECG), the blood flow rate of brain, etc.) and then each extracts characteristics that best represent properties of the respective biometric signals, integrates the extracted characteristics into one to generate data having high reliability, and simultaneously measures the respective biometric signals and then extracts characteristics that best represent properties of the respective biometric signals. After the extracted characteristics are classified by several classifiers, a final output value of these classifiers may be integrated into one.

Figure 4A:
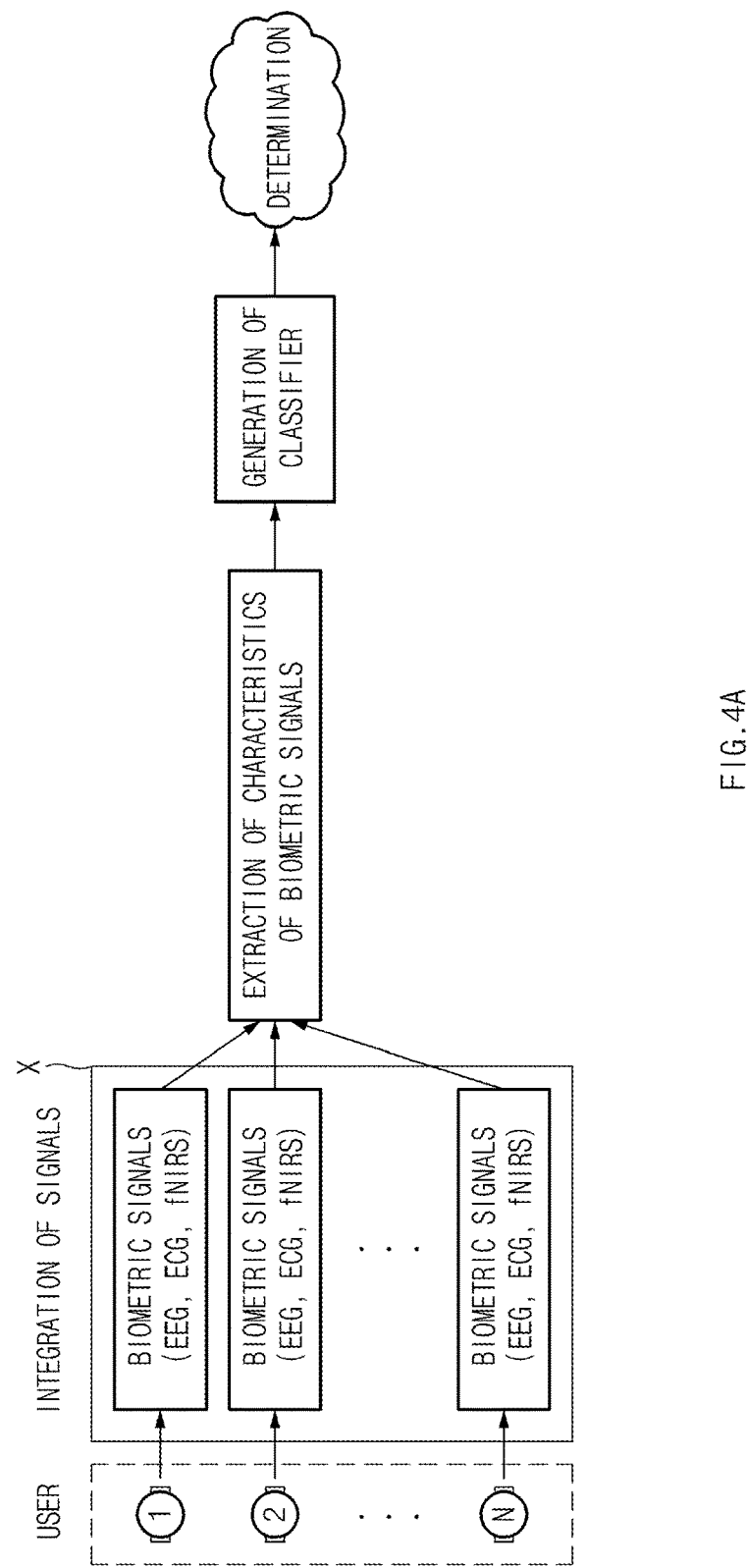
FIGS. 4A to 4C are diagrams illustrating a method for integrating multi-modality biometric signals of the biometric signal integral part within the apparatus for detecting a state of a driver.
Figure 4B:
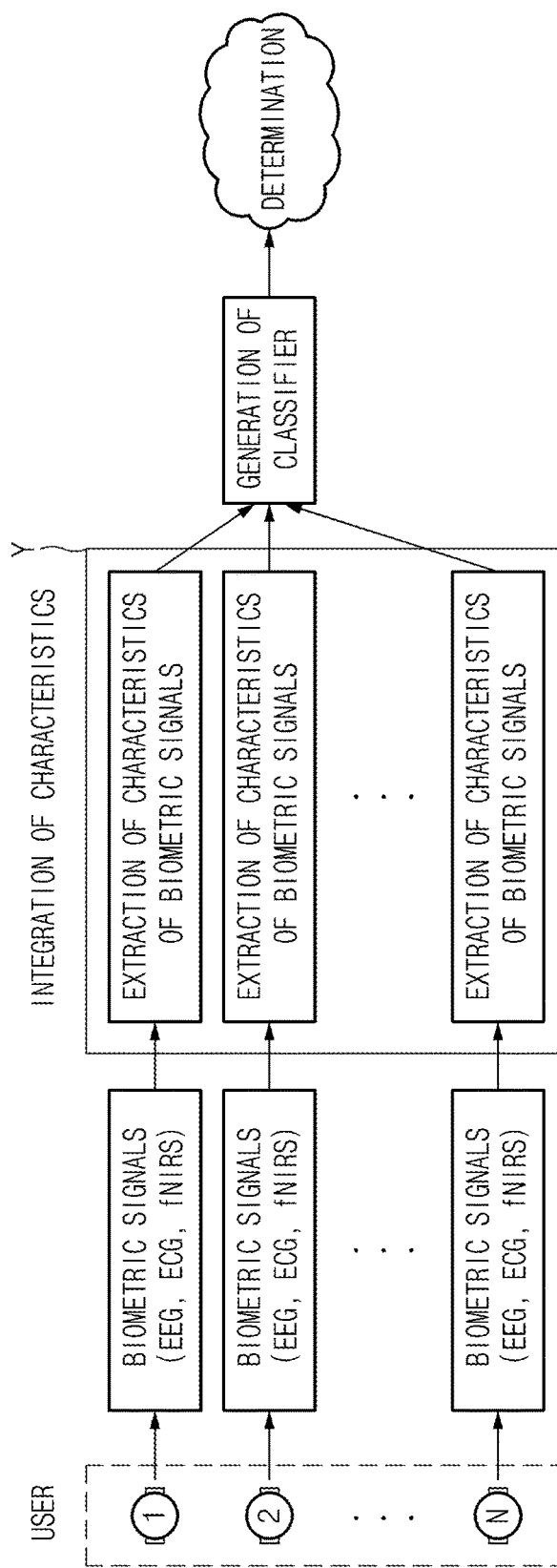
Figure 4C:
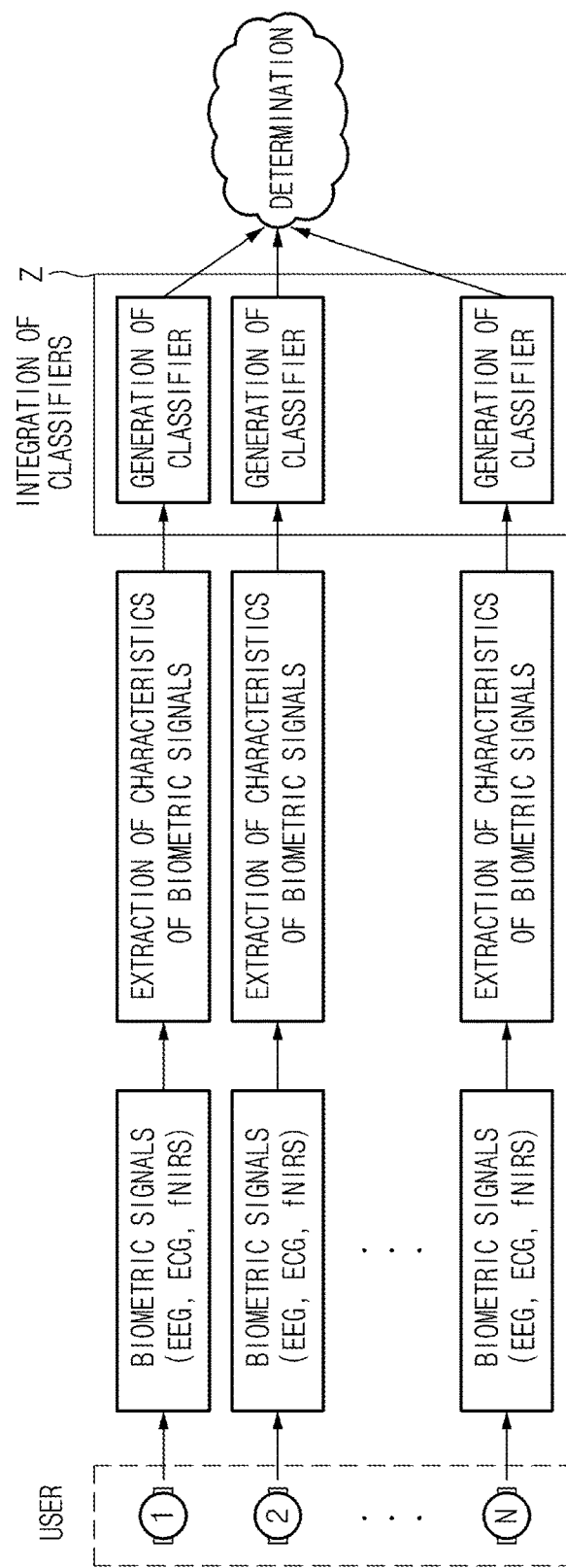

FIGS. 4A to 4C are diagrams illustrating a method for integrating multi-modality biometric signals of the biometric signal integral part within the apparatus for detecting a state of a driver according to an exemplary embodiment of the present disclosure.

Referring to FIG. 4A, the biometric signal integral part may immediately integrate X the biometric signals (raw data) measured by the biometric signal measuring part.

Referring to FIG. 4B, the biometric signal integral part may extract characteristics of the biometric signals from the biometric signals measured by the biometric signal measuring part and may then integrate Y the extracted characteristics of the biometric signals.

Referring to FIG. 4C, the biometric signal integral part may classify the extracted characteristics of the biometric signals and may then integrate Z the classified biometric signals.

Figure 5:
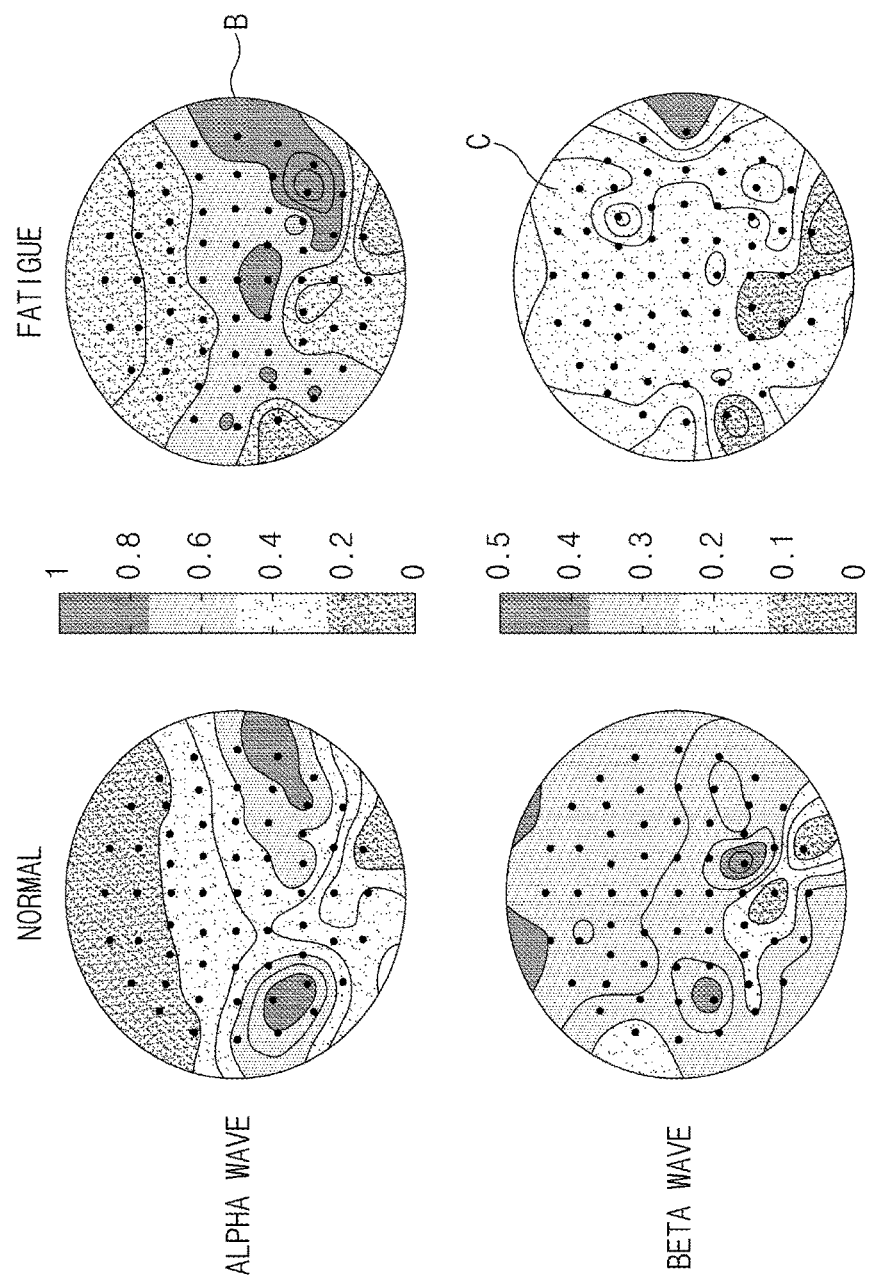
FIG. 5 is a diagram illustrating a method for extracting characteristics of an electroencephalography by the biometric signal integral part within the apparatus for detecting a state of a driver.

FIG. 5 is a diagram illustrating a method for extracting characteristics of an electroencephalography by the biometric signal integral part within the apparatus for detecting a state of a driver according to an exemplary embodiment of the present disclosure.

Referring to FIG. 5, according to the method for extracting characteristics of an electroencephalography by the biometric signal integral part within the apparatus for detecting a state of a driver, characteristics of the electroencephalography may be extracted by extracting relative power level (RPL) characteristics using electrodes attached to the scalp of the driver, converting time-series data into frequency data using Fourier transform, extracting an alpha wave (8 Hz to 13 Hz) and a beta wave (13 Hz to 30 Hz) after the conversion into the frequency data, and performing normalization by dividing the alpha wave and the beta wave with a power value of 1 Hz to 50 Hz.

For example, FIG. 5 illustrates a comparison of the EEG between a normal driver group (a normal group) and a driver group (an abnormal group or a fatigued group) that becomes artificially fatigued, and as illustrated in FIG. 5, an RPL value of the alpha wave is more significant in the driver group that becomes artificially fatigued than in the normal driver group.

FIG. 5 is a diagram viewed from the top of a head of the driver, wherein the top of the head of the driver may be referred to as a frontal lobe, a bottom thereof may be referred to as an occipital lobe, and left and right sides may be referred to as a temporal lobe.

Here, the alpha wave significantly shows in the temporal lobe B of the abnormal group (is shown by strong or dark color), and the beta wave shows to be lower in the frontal lobe C of the abnormal group.

Figure 6:
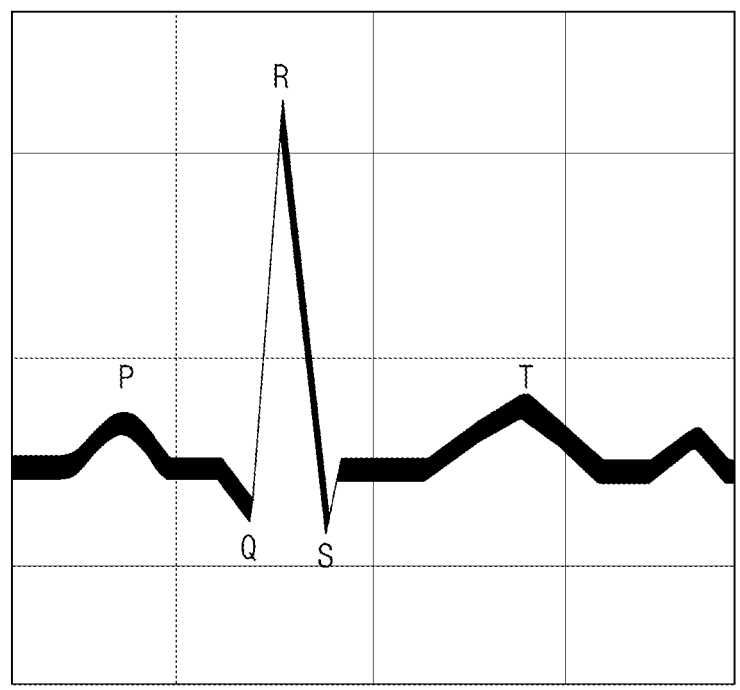
FIG. 6 is a diagram illustrating a method for extracting characteristics of an electrocardiography by the biometric signal integral part within the apparatus for detecting a state of a driver.

FIG. 6 is a diagram illustrating a method for extracting characteristics of an electrocardiography by the biometric signal integral part within the apparatus for detecting a state of a driver.

Referring to FIG. 6, according to the method for extracting characteristics of an electrocardiography by the biometric signal integral part within the apparatus for detecting a state of a driver, characteristics of the electrocardiography may be extracted by extracting a component of R among components of P, Q, R, S, and T of the electrocardiography and calculating a heart rate using the extracted component of R.

For example, the heart rate may be calculated by measuring the electrocardiography of the driver, calculating the component of R for 1 minute, and using the calculated component of R.

Figure 7:
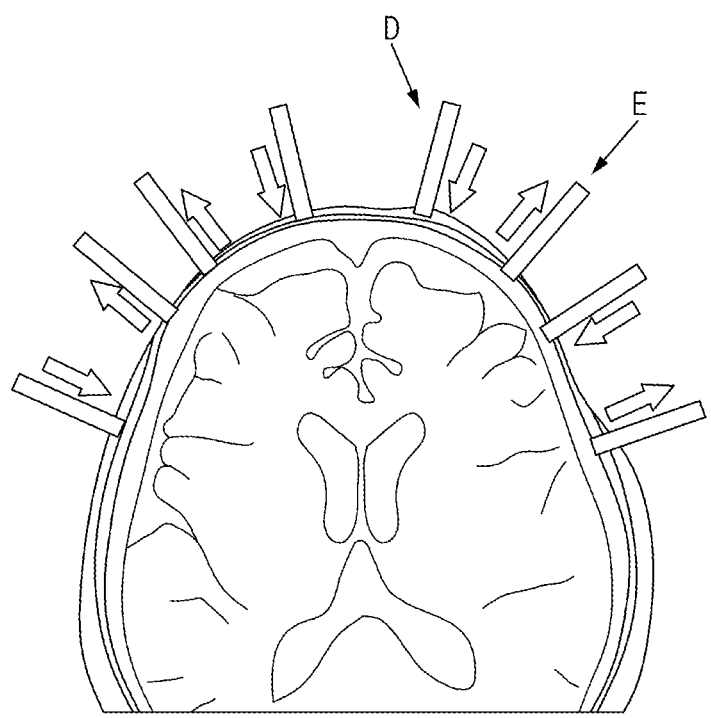
FIG. 7 is a diagram illustrating a method for extracting characteristics of a functional near-infrared spectroscopy by the biometric signal integral part within the apparatus for detecting a state of a driver.

FIG. 7 is a diagram illustrating method for extracting characteristics of functional Near-Infrared spectroscopy by the biometric signal integral part within the apparatus for detecting a state of a driver.

Referring to FIG. 7, according to forms of the method for extracting characteristics of a functional Near-Infrared spectroscopy by the biometric signal integral part within the apparatus for detecting a state of a driver, oxyhemoglobin concentration (HbO) and specific oxyhemoglobin concentration (HbR) may be detected by measuring a reflection amount by the detector, converting light intensity into the oxyhemoglobin concentration and the specific oxyhemoglobin concentration using an absorption rate of light such as modified Beer-Lambert Law (mBLL), and using oxyhemoglobin and specific oxyhemoglobin as characteristics, and the blood flow rate of the brain of the driver may be measured using the oxyhemoglobin concentration and the specific oxyhemoglobin concentration.

Specifically, in FIG. 7, the emitter D generates near-field infrared ray, and the detector E measures the near-field infrared ray which is reflected or scattered.

A value of the measured near-field infrared ray is the light intensity, and the oxyhemoglobin concentration and the specific oxyhemoglobin concentration (HbO/HbR) of the brain may be measured using Modified Beer-Lambert Law (mBLL).

Specifically, the driver state detecting part within the apparatus for detecting a state of a driver according to an exemplary embodiment of the present disclosure will describe a method for extracting a driving condition level of the driver.

According to the method for extracting a driving condition level of the driver in the driver state detecting part within the apparatus for detecting a state of a driver, values of the electro-encephalography (the alpha wave, the beta wave), the electro-cardiography (the heart rate), the blood flow rate of the brain (the oxyhemoglobin concentration) are calculated using the following Equation 1.

$$norm(x) = \frac{x - \min(x)}{\max(x) - \min(x)} \quad \text{[Equation 1]}$$

Here, norm(x) is an equation that maps three signals having magnitudes of different ranges to a value from 0 to 1, and x means characteristics extracted from the respective signals, which means the alpha wave and the beta wave in the electro-encephalography, means the heart rate in the electro-cardiography, and means the oxyhemoglobin concentration (HbO) in the blood flow rate of the brain.

Next, the driving condition level (DCL) is calculated by applying the same weight to the values of the electro-encephalography (the alpha wave, the beta wave), the electro-cardiography (the heart rate), the blood flow rate of the brain (the oxyhemoglobin concentration), which is as in the following Equation 2.

$$DCL = norm\left(\frac{\text{Beta Wave}}{\text{Alpha Wave}}\right) + \quad \text{[Equation 2]}$$

$$norm(\text{Oxyhemoglobin Concentration}) +$$

$$norm(\text{Heart Rate})$$

$$\left(\begin{array}{l} 0 \leq norm\left(\frac{\text{Beta Wave}}{\text{Alpha Wave}}\right) \leq 1.0 \leq \\ norm(\text{Oxyhemoglobin Concentration}) \leq 1 \\ 0 \leq norm(\text{Heart Rate}) \leq 1.0 \leq DCL \leq 3 \end{array}\right),$$

Figure 8:
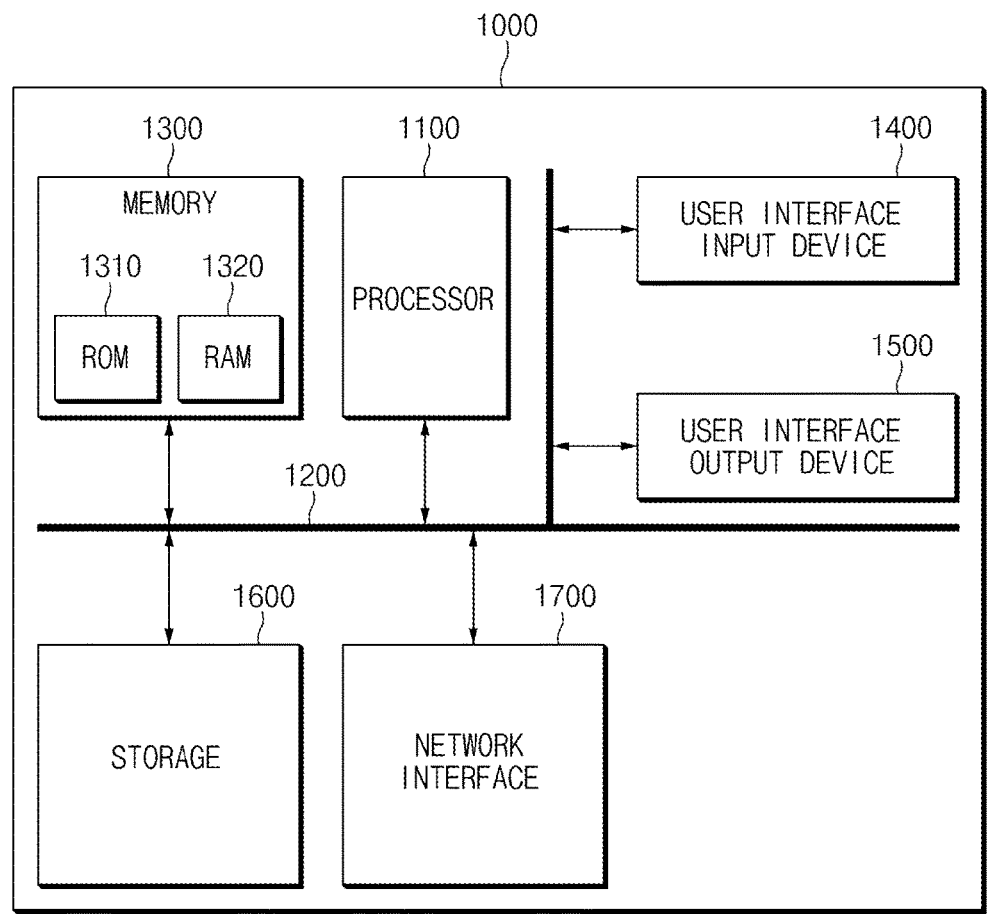
FIG. 8 is a block diagram illustrating a computing system that executes the method for detecting a state of a driver based on biometric signals of the driver according to an exemplary embodiment of the present disclosure.

FIG. 8 is a block diagram illustrating a computing system that executes the method for detecting a state of a driver based on biometric signals of the driver according to an exemplary embodiment of the present disclosure.

Referring to FIG. 8, a computing system 1000 may include at least one processor 1100, a memory 1300, a user interface input device 1400, a user interface output device 1500, a storage 1600, and a network interface 1700 which are connected through a bus 1200.

The processor 1100 may be a central processing unit (CPU) or a semiconductor device executing processes for instructions which are stored in the memory 1300 and/or the storage 1600. The memory 1300 and the storage 1600 may include various kinds of volatile or non-volatile storing media. For example, the memory 1300 may include a read only memory (ROM) and a random access memory (RAM).

Accordingly, steps in the method or algorithm which is described in connection with the exemplary embodiments disclosed in the present specification may be directly implemented in hardware, a software module, or a combination thereof which is executed by the processor 1100. The software module may be resided on a storing medium (i.e., the memory 1300 and/or the storage 1600) such as a random access memory (RAM) memory, a flash memory, a read only memory (ROM) memory, an erasable programmable read only memory (EPROM) memory, an electrically erasable programmable read only memory (EEPROM) memory, a register, a hard disk, a removable disk, or a compact disc-read only memory (CD-ROM). An illustrative storing medium may be coupled to the processor 1100 and the processor 1100 may read information from the storing medium and write the information into the storing medium. Alternatively, the storing medium may also be integral with the processor 1100. The processor and the storing medium may also be resided within an application specific integrated circuit (ASIC). The ASIC may also be resided within a user terminal. Alternatively, the processor and the storing medium may also be resided within the user terminal as an individual component.

As described above, according to the exemplary forms of the present disclosure, the apparatus and the method for detecting biometric signals of a driver may classify and analyze the driver into the normal state and the fatigued state using the blood flow rate of brain, the electro-encephalography (EEG), and the electro-cardiography (ECG) of the driver to thereby quantify the fatigue level of the driver using the analyzed biometric signals.

Hereinabove, although the present disclosure has been described with reference to exemplary forms and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. An apparatus for detecting a state of a driver based on biometric signals of the driver executed by a processor, the apparatus comprising:
   a biometric signal measuring part configured to measure the biometric signals including a blood flow rate of a brain of the driver by using an electro-encephalography (EEG), an electro-cardiography (ECG), and a functional near-infrared spectroscopy (fNIRS) of the driver;
   a biometric signal integral part configured to analyze and integrate the measured biometric signals of the driver, to extract characteristics of the respective biometric signals from the measured biometric signals and then to integrate the extracted characteristics, or to classify the extracted characteristics of the biometric signals and then to integrate the classified characteristics;
   a driver state detecting part configured to detect the state of the driver based on the integrated biometric signals; and
   wherein the processor is configured to classify and analyze the driver into a normal state and a fatigue state based on the measured biometric signals.

2. The apparatus according to claim 1, wherein the biometric signal measuring part includes:
   an electro-encephalography measuring apparatus configured to measure the electro-encephalography occurring from the brain;
   an emitter configured to generate near-field infrared ray to measure the blood flow rate of the brain; and
   a detector configured to detect the near-field infrared ray reflected after the emitter generates the near-field infrared ray and to obtain electrical signals.

3. The apparatus according to claim 1, wherein to extract characteristics of the respective biometric signals are from the measured biometric signals, the biometric signal integral part is configured to extract characteristics of the electro-encephalography by extracting characteristics of a relative power level (RPL) using electrodes attached to a scalp of the driver.

4. The apparatus according to claim 1, wherein when characteristics of the respective biometric signals are extracted from the measured biometric signals, the biometric signal integral part is configured to extract characteristics of the electro-cardiography by extracting a component of R among components of P, Q, R, S, and T of the electro-cardiography and to calculate a heart rate using the extracted component of R.

5. The apparatus according to claim 1, wherein when characteristics of the respective biometric signals are extracted from the measured biometric signals, the biometric signal measuring part is configured to measure the blood flow rate of the brain of the driver by measuring a reflection amount by a detector, converting light intensity into oxyhemoglobin and specific oxyhemoglobin concentrations using an absorption rate of light, and using the oxyhemoglobin and specific oxyhemoglobin concentrations.

6. The apparatus according to claim 1, wherein the driver state detecting part is configured to calculate a driving condition level by applying a same weight to values of the electro-encephalography, the electro-cardiography, and the blood flow rate of the brain.

7. A method for detecting a state of a driver based on biometric signals of the driver executed by a processor, the method comprising:
   measuring the biometric signals of the driver including a blood flow rate of a brain of the driver using an electro-encephalography (EEG), an electro-cardiography (ECG), and a functional near-infrared spectroscopy (fNIRS) of the driver;
   analyzing and integrating the measured biometric signals of the driver, extracting characteristics of the respective biometric signals from the measured biometric signals and then integrating the extracted characteristics, or classifying the extracted characteristics of the biometric signals and then integrating the classified characteristics;
   detecting the state of the driver based on the integrated biometric signals; and
   classifying and analyzing the driver into a normal state and a fatigue state based on the measured biometric signals.

8. The method according to claim 7, wherein when characteristics of the respective biometric signals are extracted from the measured biometric signals, characteristics of the electro-encephalography are extracted by extracting characteristics of a relative power level (RPL) using electrodes attached to a scalp of the driver.

9. The method according to claim 7, wherein when characteristics of the respective biometric signals are extracted from the measured biometric signals, characteristics of the electro-cardiography are extracted by extracting a component of R among components of P, Q, R, S, and T of the electro-cardiography and calculating a heart rate using the extracted component of R.

10. The method according to claim 7, wherein when characteristics of the respective biometric signals are extracted from the measured biometric signals, the blood flow rate of the brain of the driver is measured by measuring a reflection amount by a detector, converting light intensity into oxyhemoglobin and specific oxyhemoglobin concentrations using an absorption rate of light, and using the oxyhemoglobin and specific oxyhemoglobin concentrations.

11. The method according to claim 7, wherein a driving condition level is calculated by applying a same weight to values of the electro-encephalography, the electro-cardiography, and the blood flow rate of the brain.

* * * * *